United States Patent

Corbin et al.

[11] Patent Number: 5,558,862
[45] Date of Patent: Sep. 24, 1996

[54] METHOD OF CONTROLLING INSECTS

[75] Inventors: David R. Corbin, Chesterfield; John T. Greenplate, Manchester; Michael G. Jennings, Chesterfield; John P. Purcell, Ballwin; Robert D. Sammons, New Melle, all of Mo.

[73] Assignee: Monsanto Company, St. Louis, Mo.

[21] Appl. No.: 475,694

[22] Filed: Jun. 7, 1995

Related U.S. Application Data

[60] Continuation-in-part of Ser. No. 393,785, Feb. 24, 1995, which is a division of Ser. No. 83,948, Jun. 28, 1993, Pat. No. 5,518,908, which is a continuation-in-part of Ser. No. 937,195, Sep. 4, 1992, abandoned, which is a continuation-in-part of Ser. No. 762,682, Sep. 23, 1991, abandoned.

[51] Int. Cl.$^6$ .............. A61K 38/44; C12N 9/02; C12N 1/20; C07H 21/04
[52] U.S. Cl. ............ 424/94.4; 435/189; 435/252.2; 435/252.3; 435/252.31; 435/252.34; 514/12; 536/23.2; 800/205
[58] Field of Search ............... 424/94.4; 514/12; 800/205; 435/189, 252.2, 252.3, 252.31, 252.34; 536/23.2

[56] References Cited

U.S. PATENT DOCUMENTS 5,518,908   5/1996   Corbin et al. ................ 435/172.3

FOREIGN PATENT DOCUMENTS

WO95/01098   1/1995   WIPO.

OTHER PUBLICATIONS

Cho et al. (1995) Appl. Microbiol. Biotechnol. 44(1–2): 133–138.
Corbin et al. (1994) Appl. Enviorn. Microbiol. 60(12):4239–4244.
Horii et al. (1990) J. Bact. 172(7): 3644–3653.
Purcell et al. (1993) Biochem. Biophys. Res. Comm. 196(3): 1406–1413.

*Primary Examiner*—Robert A. Wax
*Assistant Examiner*—Lisa J. Hobbs
*Attorney, Agent, or Firm*—Grace L. Bonner; Carol Clayman; Dennis R. Hoerner, Jr.

[57] ABSTRACT

3-Hydroxysteroid oxidase controls insects, particularly lepidopteran and boll weevil. Genes encoding for this enzyme may be cloned into vectors for transformation of plant-colonizing microorganisms, thereby providing a method of controlling insect infestation.

21 Claims, No Drawings

5,558,862

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Val Ser Thr Leu Met Leu Glu Met Gly Gln Leu Trp Asn Gln Pro
1               5                   10                  15

( 2 ) INFORMATION FOR SEQ ID NO:2:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Ala Phe Ala Asp Asp Phe Cys Tyr His Pro Leu Gly Gly Cys Val Leu
1               5                   10                  15

( 2 ) INFORMATION FOR SEQ ID NO:3:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Asn Leu Tyr Val Thr Asp Gly Ser Leu Ile Pro Gly
1               5                   10

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GTGTCCACCC TGATGCTGGA GATGGGCCAG CTGTGGAACC AGCCC            45

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCTTCGCCG ACGACTTCTG CTACCACCCG CTCGGCGGCT GCGTCCTG         48

( 2 ) INFORMATION FOR SEQ ID NO:6:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

AACCTCTACG TGACCGACGG TTCGCTGATC CCGGGT 36

(2) INFORMATION FOR SEQ ID NO:7:

(i) SEQUENCE CHARACTERISTICS:
        (A) LENGTH: 1865 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

| | | | | | | |
|---|---|---|---|---|---|---|
| CTACTCCATG | GCGTGCTGAA | GGTCGGTGCC | TGGCCTCCCG | AGGTCGTCGA | GGACTTCGTG | 60 |
| AAGTGAGCGG | GCACCCCGCC | CGTCCCCGCC | CCGCAACGGC | CCGTTCCGCA | CACCGGGTGA | 120 |
| CCCGACCCCC | TCGGCCCCCG | ACGTCCGCCG | ACCTCTCAGT | CCCCTCTCGA | AGCTCAGGAG | 180 |
| CAACAGCGTG | AACGCACACC | AGCCTCTGTC | GCGCCGCCGC | ATGCTCGGCC | TGGCCGCCTT | 240 |
| GGGCGCCGCC | GCACTCACCG | GCAGACCAC | GATCACCGCG | GCCCCCGCG | CGGCCGCCGC | 300 |
| CACCGCCCCC | GGCGGCTCCG | GCGGCACGTT | CGTGCCCGCC | GTCGTGATCG | GCACCGGCTA | 360 |
| CGGCGCGGCC | GTCTCCGCCC | TGCGGCTCGG | CGAGGCCGGG | GTCTCCACCC | TGATGCTGGA | 420 |
| GATGGGCCAG | CTGTGGAACC | AGCCCGGCCC | GGACGGCAAC | GTCTTCTGCG | GATGCTCAA | 480 |
| GCCCGACAAG | CGCTCCAGCT | GGTTCAAGAC | CCGCACCGAG | GCCCCGCTCG | GCTCCTTCCT | 540 |
| CTGGCTCGAC | CTCGCCAACC | GGGACATCGA | CCCCTACGCG | GGCGTCCTGG | ACCGGGTCAA | 600 |
| CTTCGACCAG | ATGTCCGTGT | ACGTGGGCCG | CGGGGTCGGC | GGCGGCTCGC | TCGTCAACGG | 660 |
| CGGTATGGCC | GTCACGCCCC | GGCGCTCCTA | CTTCCAGGAG | GTGCTGCCCC | AGGTCGACGC | 720 |
| CGACGAGATG | TACGGCACCT | ACTTCCCGCG | CGCGAACTCC | GGCCTGCGGG | TCAACAACAT | 780 |
| CGACAAGGAC | TGGTTCGAGC | AGACCGAGTG | GTACACGTTC | GCGCGCGTTG | CCCGTCTGCA | 840 |
| GGCCGAGAAC | GCCGGCCTGA | AGACCACCTT | CGTGCCCAAC | GTCTACGACT | GGGACTACAT | 900 |
| GCGCGGTGAG | GCGGACGGCA | CCAACCCCAA | GTCCGCGCTC | GCCGCCGAGG | TCATCTACGG | 960 |
| CAACAACCAC | GGCAAGGTCT | CCCTCGACAA | GAGCTACCTG | GCGGCCGCCC | TGGGCACCGG | 1020 |
| CAAGGTCACC | GTCGAGACCC | TGCACCAGGT | CAAGACGATC | CGTCAGCAGA | ACGACGGCAC | 1080 |
| CTACCTGCTG | ACGGTCGAGC | AGAAGGACCC | CGACGGCAAG | CTGCTCGGGA | CCAAGGAGAT | 1140 |
| CTCCTGCCGC | CACCTCTTCC | TCGGCGCCGG | CAGCCTCGGC | TCCATTGAAC | TGCTGCTGCG | 1200 |
| CGCCCGGGAG | ACCGGCACCC | TGCCCGGCCT | CAGCTCCGAG | ATCGGCGGCG | CTGGGGCCC | 1260 |
| CAACGGCAAC | ATCATGACCG | CCCGCGCCAA | CCATGTGTGG | AACCCCACGG | GCAGCAAGCA | 1320 |
| GTCGTCGATC | CCCGCCCTCG | GCATCGACGA | CTGGGACAAC | CCCGACAACC | CCGTCTTCGC | 1380 |
| CGAGATAGCC | CCCATGCCGG | CGGGCCTCGA | GACCTGGGTC | AGCCTCTACC | TGGCCATCAC | 1440 |
| CAAGAACCCG | GAGCGCGGCA | CCTTCGTCTA | CGACGCCGCC | AAGGACCGGG | CGGACCTGCG | 1500 |
| CTGGACCCGG | GACCAGAACG | CGCCCGCGGT | CGCCGCCGCC | AAGTCGCTGT | TCGACCGCGT | 1560 |
| CAACAAGGCC | AACACGACCA | TCTACCGGTA | CGACCTCTTC | GGCAAGCAGA | TCAAGGCGTT | 1620 |
| CGCCGACGAC | TTCTGCTACC | ACCCGCTCGG | CGGCTGCGTC | CTCGGCAAGG | CCACCGACAA | 1680 |
| CTACGGCCGC | GTCTCCGGGT | ACAAGAACCT | CTACGTCACC | GACGGCTCGC | TCATCCCCGG | 1740 |
| CAGCATCGGC | GTCAACCCGT | TCGTGACCAT | CACGGCGCTG | GCGGAGCGGA | ACGTCGAGCG | 1800 |
| CGTCATCAAG | GAGGACATCG | CGGGTTCCTG | ACGAGCGACG | GGCGGGGCGC | GGCATGCAAG | 1860 |
| CTTGG | | | | | | 1865 |

( 2 ) INFORMATION FOR SEQ ID NO:8:

( i ) SEQUENCE CHARACTERISTICS:
        ( A ) LENGTH: 547 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Val Asn Ala His Gln Pro Leu Ser Arg Arg Arg Met Leu Gly Leu Ala
 1               5                  10                  15

Ala Leu Gly Ala Ala Ala Leu Thr Gly Gln Thr Thr Ile Thr Ala Ala
            20                  25                  30

Pro Arg Ala Ala Ala Ala Thr Ala Pro Gly Gly Ser Gly Gly Thr Phe
        35                  40                  45

Val Pro Ala Val Val Ile Gly Thr Gly Tyr Gly Ala Ala Val Ser Ala
    50                  55                  60

Leu Arg Leu Gly Glu Ala Gly Val Ser Thr Leu Met Leu Glu Met Gly
65                  70                  75                  80

Gln Leu Trp Asn Gln Pro Gly Pro Asp Gly Asn Val Phe Cys Gly Met
                85                  90                  95

Leu Lys Pro Asp Lys Arg Ser Ser Trp Phe Lys Thr Arg Thr Glu Ala
            100                 105                 110

Pro Leu Gly Ser Phe Leu Trp Leu Asp Leu Ala Asn Arg Asp Ile Asp
        115                 120                 125

Pro Tyr Ala Gly Val Leu Asp Arg Val Asn Phe Asp Gln Met Ser Val
    130                 135                 140

Tyr Val Gly Arg Gly Val Gly Gly Gly Ser Leu Val Asn Gly Gly Met
145                 150                 155                 160

Ala Val Thr Pro Arg Arg Ser Tyr Phe Gln Glu Val Leu Pro Gln Val
                165                 170                 175

Asp Ala Asp Glu Met Tyr Gly Thr Tyr Phe Pro Arg Ala Asn Ser Gly
            180                 185                 190

Leu Arg Val Asn Asn Ile Asp Lys Asp Trp Phe Glu Gln Thr Glu Trp
        195                 200                 205

Tyr Thr Phe Ala Arg Val Ala Arg Leu Gln Ala Glu Asn Ala Gly Leu
    210                 215                 220

Lys Thr Thr Phe Val Pro Asn Val Tyr Asp Trp Asp Tyr Met Arg Gly
225                 230                 235                 240

Glu Ala Asp Gly Thr Asn Pro Lys Ser Ala Leu Ala Ala Glu Val Ile
                245                 250                 255

Tyr Gly Asn Asn His Gly Lys Val Ser Leu Asp Lys Ser Tyr Leu Ala
            260                 265                 270

Ala Ala Leu Gly Thr Gly Lys Val Thr Val Glu Thr Leu His Gln Val
        275                 280                 285

Lys Thr Ile Arg Gln Gln Asn Asp Gly Thr Tyr Leu Leu Thr Val Glu
    290                 295                 300

Gln Lys Asp Pro Asp Gly Lys Leu Leu Gly Thr Lys Glu Ile Ser Cys
305                 310                 315                 320

Arg His Leu Phe Leu Gly Ala Gly Ser Leu Gly Ser Ile Glu Leu Leu
                325                 330                 335

Leu Arg Ala Arg Glu Thr Gly Thr Leu Pro Gly Leu Ser Ser Glu Ile
            340                 345                 350

Gly Gly Gly Trp Gly Pro Asn Gly Asn Ile Met Thr Ala Arg Ala Asn
        355                 360                 365
```

| | | | | | | | | | | | | | | |
|---|---|---|---|---|---|---|---|---|---|---|---|---|---|---|
|His|Val|Trp|Asn|Pro|Thr|Gly|Ser|Lys|Gln|Ser|Ser|Ile|Pro|Ala|Leu|
| |370| | | | |375| | | |380| | | | |
|Gly|Ile|Asp|Asp|Trp|Asp|Asn|Pro|Asp|Asn|Pro|Val|Phe|Ala|Glu|Ile|
|385| | | | |390| | | |395| | | | | |400|
|Ala|Pro|Met|Pro|Ala|Gly|Leu|Glu|Thr|Trp|Val|Ser|Leu|Tyr|Leu|Ala|
| | | | |405| | | | |410| | | | |415| |
|Ile|Thr|Lys|Asn|Pro|Glu|Arg|Gly|Thr|Phe|Val|Tyr|Asp|Ala|Ala|Lys|
| | | |420| | | | |425| | | | |430| | |
|Asp|Arg|Ala|Asp|Leu|Arg|Trp|Thr|Arg|Asp|Gln|Asn|Ala|Pro|Ala|Val|
| | |435| | | | |440| | | |445| | | | |
|Ala|Ala|Ala|Lys|Ser|Leu|Phe|Asp|Arg|Val|Asn|Lys|Ala|Asn|Thr|Thr|
| |450| | | | |455| | | |460| | | | | |
|Ile|Tyr|Arg|Tyr|Asp|Leu|Phe|Gly|Lys|Gln|Ile|Lys|Ala|Phe|Ala|Asp|
|465| | | | |470| | | |475| | | | | |480|
|Asp|Phe|Cys|Tyr|His|Pro|Leu|Gly|Gly|Cys|Val|Leu|Gly|Lys|Ala|Thr|
| | | | |485| | | |490| | | | |495| | |
|Asp|Asn|Tyr|Gly|Arg|Val|Ser|Gly|Tyr|Lys|Asn|Leu|Tyr|Val|Thr|Asp|
| | | |500| | | |505| | | | |510| | | |
|Gly|Ser|Leu|Ile|Pro|Gly|Ser|Ile|Gly|Val|Asn|Pro|Phe|Val|Thr|Ile|
| | |515| | | |520| | | | |525| | | | |
|Thr|Ala|Leu|Ala|Glu|Arg|Asn|Val|Glu|Arg|Val|Ile|Lys|Glu|Asp|Ile|
| |530| | | |535| | | | |540| | | | | |
|Ala|Gly|Ser| | | | | | | | | | | | | |
|545| | | | | | | | | | | | | | | |

( 2 ) INFORMATION FOR SEQ ID NO:9:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

CTCAGGAGCA CCATGGCGAC CGCACAC 27

( 2 ) INFORMATION FOR SEQ ID NO:10:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GTGCCGCCGG AGGCCATGGG GGCGGTGGC 29

( 2 ) INFORMATION FOR SEQ ID NO:11:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:11:

| | | | | | |
|---|---|---|---|---|---|
| GCCCCGCCCG | TCGGATCCGT | CAGGAACCCG | | | 30 |

(2) INFORMATION FOR SEQ ID NO:12:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (xi) SEQUENCE DESCRIPTION: SEQ ID NO:12:

Ser  Gly  Gly  Thr  Phe
    1                      5

(2) INFORMATION FOR SEQ ID NO:13:

(i) SEQUENCE CHARACTERISTICS:
        (A) LENGTH: 1647 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

| | | | | | |
|---|---|---|---|---|---|
| ATGGCGACCG | CACACCAGCC | TCTGTCGCGC | CGCCGCATGC | TCGGCCTGGC | CGCCTTGGGC | 60 |
| GCCGCCGCAC | TCACCGGGCA | GACCACGATC | ACCGCGGCCC | CCGCGCGGC | CGCCGCCACC | 120 |
| GCCCCGGCG | GCTCCGGCGG | CACGTTCGTG | CCCGCCGTCG | TGATCGGCAC | CGGCTACGGC | 180 |
| GCGGCCGTCT | CCGCCCTGCG | GCTCGGCGAG | GCCGGGGTCT | CCACCCTGAT | GCTGGAGATG | 240 |
| GGCCAGCTGT | GGAACCAGCC | CGGCCCGGAC | GGCAACGTCT | TCTGCGGGAT | GCTCAAGCCC | 300 |
| GACAAGCGCT | CCAGCTGGTT | CAAGACCCGC | ACCGAGGCCC | CGCTCGGCTC | CTTCCTCTGG | 360 |
| CTCGACCTCG | CCAACCGGGA | CATCGACCCC | TACGCGGGCG | TCCTGGACCG | GGTCAACTTC | 420 |
| GACCAGATGT | CCGTGTACGT | GGGCCGCGGG | GTCGGCGGCG | GCTCGCTCGT | CAACGGCGGT | 480 |
| ATGGCCGTCA | CGCCCCGGCG | CTCCTACTTC | CAGGAGGTGC | TGCCCCAGGT | CGACGCCGAC | 540 |
| GAGATGTACG | GCACCTACTT | CCCGCGCGCG | AACTCCGGCC | TGCGGGTCAA | CAACATCGAC | 600 |
| AAGGACTGGT | TCGAGCAGAC | CGAGTGGTAC | ACGTTCGCGC | GCGTTGCCCG | TCTGCAGGCC | 660 |
| GAGAACGCCG | GCCTGAAGAC | CACCTTCGTG | CCCAACGTCT | ACGACTGGGA | CTACATGCGC | 720 |
| GGTGAGGCGG | ACGGCACCAA | CCCCAAGTCC | GCGCTCGCCG | CCGAGGTCAT | CTACGGCAAC | 780 |
| AACCACGGCA | AGGTCTCCCT | CGACAAGAGC | TACCTGGCGG | CCGCCCTGGG | CACCGGCAAG | 840 |
| GTCACCGTCG | AGACCCTGCA | CCAGGTCAAG | ACGATCCGTC | AGCAGAACGA | CGGCACCTAC | 900 |
| CTGCTGACGG | TCGAGCAGAA | GGACCCCGAC | GGCAAGCTGC | TCGGGACCAA | GGAGATCTCC | 960 |
| TGCCGCCACC | TCTTCCTCGG | CGCCGGCAGC | CTCGGCTCCA | TTGAACTGCT | GCTGCGCGCC | 1020 |
| CGGGAGACCG | GCACCCTGCC | CGGCCTCAGC | TCCGAGATCG | GCGGCGGCTG | GGGCCCCAAC | 1080 |
| GGCAACATCA | TGACCGCCCG | CGCCAACCAT | GTGTGGAACC | CCACGGGCAG | CAAGCAGTCG | 1140 |
| TCGATCCCCG | CCCTCGGCAT | CGACGACTGG | GACAACCCCG | ACAACCCCGT | CTTCGCCGAG | 1200 |
| ATAGCCCCCA | TGCCGGCGGG | CCTCGAGACC | TGGGTCAGCC | TCTACCTGGC | CATCACCAAG | 1260 |
| AACCCGGAGC | GCGGCACCTT | CGTCTACGAC | GCCGCCAAGG | ACCGGGCGGA | CCTGCGCTGG | 1320 |
| ACCCGGGACC | AGAACGCGCC | CGCGGTCGCC | GCCGCCAAGT | CGCTGTTCGA | CCGCGTCAAC | 1380 |
| AAGGCCAACA | CGACCATCTA | CCGGTACGAC | CTCTTCGGCA | AGCAGATCAA | GGCGTTCGCC | 1440 |
| GACGACTTCT | GCTACCACCC | GCTCGGCGGC | TGCGTCCTCG | GCAAGGCCAC | CGACAACTAC | 1500 |

| | | | | | | |
|---|---|---|---|---|---|---|
| GGCCGCGTCT | CCGGGTACAA | GAACCTCTAC | GTCACCGACG | GCTCGCTCAT | CCCCGGCAGC | 1560 |
| ATCGGCGTCA | ACCCGTTCGT | GACCATCACG | GCGCTGGCGG | AGCGGAACGT | CGAGCGCGTC | 1620 |
| ATCAAGGAGG | ACATCGCGGG | TTCCTGA | | | | 1647 |

( 2 ) INFORMATION FOR SEQ ID NO:14:

( i ) SEQUENCE CHARACTERISTICS:
        ( A ) LENGTH: 1521 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:14:

| | | | | | | |
|---|---|---|---|---|---|---|
| ATGGCCTCCG | GCGGCACGTT | CGTGCCCGCC | GTCGTGATCG | GCACCGGCTA | CGGCGCGGCC | 60 |
| GTCTCCGCCC | TGCGGCTCGG | CGAGGCCGGG | GTCTCCACCC | TGATGCTGGA | GATGGGCCAG | 120 |
| CTGTGGAACC | AGCCCGGCCC | GGACGGCAAC | GTCTTCTGCG | GGATGCTCAA | GCCCGACAAG | 180 |
| CGCTCCAGCT | GGTTCAAGAC | CCGCACCGAG | GCCCGCTCG | GCTCCTTCCT | CTGGCTCGAC | 240 |
| CTCGCCAACC | GGGACATCGA | CCCCTACGCG | GGCGTCCTGG | ACCGGGTCAA | CTTCGACCAG | 300 |
| ATGTCCGTGT | ACGTGGGCCG | CGGGGTCGGC | GGCGGCTCGC | TCGTCAACGG | CGGTATGGCC | 360 |
| GTCACGCCCC | GGCGCTCCTA | CTTCCAGGAG | GTGCTGCCCC | AGGTCGACGC | CGACGAGATG | 420 |
| TACGGCACCT | ACTTCCCGCG | CGCGAACTCC | GGCCTGCGGG | TCAACAACAT | CGACAAGGAC | 480 |
| TGGTTCGAGC | AGACCGAGTG | GTACACGTTC | GCGCGCGTTG | CCCGTCTGCA | GGCCGAGAAC | 540 |
| GCCGGCCTGA | AGACCACCTT | CGTGCCCAAC | GTCTACGACT | GGGACTACAT | GCGCGGTGAG | 600 |
| GCGGACGGCA | CCAACCCCAA | GTCCGCGCTC | GCCGCCGAGG | TCATCTACGG | CAACAACCAC | 660 |
| GGCAAGGTCT | CCCTCGACAA | GAGCTACCTG | GCGGCCGCCC | TGGGCACCGG | CAAGGTCACC | 720 |
| GTCGAGACCC | TGCACCAGGT | CAAGACGATC | CGTCAGCAGA | ACGACGGCAC | CTACCTGCTG | 780 |
| ACGGTCGAGC | AGAAGGACCC | CGACGGCAAG | CTGCTCGGGA | CCAAGGAGAT | CTCCTGCCGC | 840 |
| CACCTCTTCC | TCGGCGCCGG | CAGCCTCGGC | TCCATTGAAC | TGCTGCTGCG | CGCCCGGGAG | 900 |
| ACCGGCACCC | TGCCCGGCCT | CAGCTCCGAG | ATCGGCGGCG | GCTGGGGCCC | CAACGGCAAC | 960 |
| ATCATGACCG | CCCGCGCCAA | CCATGTGTGG | AACCCCACGG | GCAGCAAGCA | GTCGTCGATC | 1020 |
| CCCGCCCTCG | GCATCGACGA | CTGGGACAAC | CCCGACAACC | CCGTCTTCGC | CGAGATAGCC | 1080 |
| CCCATGCCGG | CGGGCCTCGA | GACCTGGGTC | AGCCTCTACC | TGGCCATCAC | CAAGAACCCG | 1140 |
| GAGCGCGGCA | CCTTCGTCTA | CGACGCCGCC | AAGGACGGG | CGGACCTGCG | CTGGACCCGG | 1200 |
| GACCAGAACG | CGCCCGCGGT | CGCCGCCGCC | AAGTCGCTGT | TCGACCGCGT | CAACAAGGCC | 1260 |
| AACACGACCA | TCTACCGGTA | CGACCTCTTC | GGCAAGCAGA | TCAAGGCGTT | CGCCGACGAC | 1320 |
| TTCTGCTACC | ACCCGCTCGG | CGGCTGCGTC | CTCGGCAAGG | CCACCGACAA | CTACGGCCGC | 1380 |
| GTCTCCGGGT | ACAAGAACCT | CTACGTCACC | GACGGCTCGC | TCATCCCCGG | CAGCATCGGC | 1440 |
| GTCAACCCGT | TCGTGACCAT | CACGGCGCTG | GCGGAGCGGA | ACGTCGAGCG | CGTCATCAAG | 1500 |
| GAGGACATCG | CGGGTTCCTG | A | | | | 1521 |

METHOD OF CONTROLLING INSECTS

This is a continuation-in-part of U.S. Ser. No. 08/393,785, filed on Feb. 24, 1995, which is a divisional application of U.S. Ser. No. 08/083,948, filed on Jun. 28, 1993, now U.S. Pat. No. 5,518,908, which is a continuation-in-part of U.S. Ser. No. 07/937,195, filed Sep. 4, 1992, now abandoned, which is a continuation-in-part of U.S. Ser. No. 07/762,682, filed Sep. 23, 1991, now abandoned.

FIELD OF THE INVENTION

This invention relates to a method of controlling insects, including lepidopteran and boll weevil, by use of an enzyme which may be applied directly to the plant or produced thereon by micro-organisms or by genetically modifying the cotton plant to produce the enzyme, and to genes, microorganisms, and plants useful in that method.

BACKGROUND OF THE INVENTION

The use of natural products, including proteins, is a well known method of controlling many insect pests. For example, endotoxins of *Bacillus thuringiensis* (B.t.) are used to control both lepidopteran and coleopteran insect pests. Genes producing these endotoxins have been introduced into and expressed by various plants, including cotton, tobacco, and tomato, and have been introduced into and expressed by various plant-colonizing microorganisms. Publications describing means for transforming such microorganisms with genes encoding and able to express *B.t.* proteins in such microorganisms include Obukowicz et al., 1986 (*J. Bacteriol.* 168: 982–989), Obukowicz et al., 1986 (*Gene* 45: 327–331), and U.S. Pat. No. 5,229,112, Obukowicz et al., issued Jul. 20, 1993. Other publications describing the transformation of various bacteria with genes encoding insecticidally active proteins include U.S. Pat. No. 4,940,840, issued Jul. 10, 1990 by Suslow, T. V. and Jones, J. D. G. and PCT Publication Number WO 95/02058, published on 19 January 1995.

There are, however, several economically important insect pests that are not susceptible to *B.t.* endotoxins. One such important pest is the cotton boll weevil. There is also a need for additional proteins which control insects for which *B.t.* provides control in order to manage any development of resistance in the population.

It is therefore an object of the present invention to provide proteins capable of controlling insects, such as boll weevil and lepidopterans, and genes useful in producing such proteins. It is a further object of the present invention to provide genetic constructs for and methods of inserting such genetic material into microorganisms. It is another object of the present invention to provide transformed microorganisms containing such genetic material.

SUMMARY OF THE INVENTION

It has been discovered that proteins that catalyze the oxidation of 3-hydroxysteroids, for example, cholesterol, will control lepidopteran insects and boll weevils. They are lethal to boll weevil larvae and will interrupt the reproductive cycle of adults. They cause mortality and stunting of larvae of lepidopteran insects. The enzymes may be applied directly to plants or introduced in other ways such as through the application of plant-colonizing microorganisms or by the plants themselves, which have been transformed to produce the enzymes.

3-Hydroxysteroid oxidases (E.C.1.1.3.6) are naturally produced by microorganisms such as Streptomyces sp., Pseudomonas sp., Mycobacterium sp., *Schizophyllum commune,* Nocardia sp., and Rhodococcus sp. [Smith et al., 1976, and Long et al., 1990.]. Preparations of enzymes from several different sources are available from Sigma Chemical Company, St. Louis, Mo.

New Streptomyces genes that control the expression of 3-hydroxysteroid oxidase have been isolated and sequenced. These new genes or genes from other known producers of 3-hydroxysteroid oxidase can be inserted into a transformation vector cassette which is used to transform "plant-colonizing microorganisms" which, when applied to the "plant environment" or to a plant seed, express the genes producing a 3-hydroxysteroid oxidase, thereby providing control of lepidopteran and boll weevil. Such 3-hydroxysteroid oxidase encoding genes may be inserted into plant-colonizing microorganisms which only express 3-hydroxysteroid oxidase or may be inserted into microorganisms which co-express additional proteins for the control of the same or other insects.

In accomplishing the foregoing, there is provided, in accordance with one aspect of the present invention, a method of controlling plant insect pests by applying to the plant environment or plant seed an insecticidally effective amount of protein toxin for ingestion by the insect, the improvement comprising applying to the plant environment or plant seed a plant-colonizing microorganism genetically engineered to contain and express a heterologous gene comprising a DNA sequence encoding 3-hydroxysteroid oxidase in an amount effective for controlling insect infestation.

In accordance with said aspect, there are provided heterologous genes comprising a microbial promoter operably joined to a "structural coding sequence" encoding 3-hydroxysteroid oxidase and microorganisms transformed therewith. In preferred embodiments of said aspect of the invention, said transformed microorganisms are selected from such Gram negative bacterial genera as Pseudomonas and such Gram positive bacterial genera as Bacillus.

In accordance with another aspect of the present invention, there is provided, a composition useful in controlling insect infestation of plants which composition comprises a genetically transformed plant-colonizing microorganism capable of expressing in a plant environment an insecticidally effective amount of 3-hydroxysteroid oxidase.

As used herein, the term "controlling insect infestation" means reducing the number of insects which cause reduced yield, either through mortality, retardation of larval development (stunting), or reduced reproductive efficiency.

As used herein, the term "structural coding sequence" means a DNA sequence which encodes for a polypeptide, which may be made by a microorganism or cell following transcription of the DNA to mRNA, followed by translation to the desired polypeptide.

As used herein, the term "plant-colonizing microorganism" means a microorganism capable of colonizing a "plant environment" and expressing the protein 3-hydroxysteroid oxidase in the plant environment such that the microorganisms can exist in a symbiotic or non-detrimental relationship with the plant. Examples of such plant-colonizing microorganisms are provided below.

As used herein, the term "plant environment" means the surface of the plant, e.g. leaf, stem, buds, stalk, floral parts, root surface, the "rhizosphere", i.e. the soil which surrounds and may be influenced by the roots of the plant., and/or extracellular areas within the plant itself, i.e. the plant vasculature.

DETAILED DESCRIPTION OF THE INVENTION

3-Hydroxysteroid oxidases catalyze the oxidation of the 3-hydroxy group of 3-hydroxysteroids to produce ketosteroids and hydrogen peroxide. They are capable of catalyzing the oxidation of various 3-hydroxysteroids, such as, for example, cholesterol. Most of the previously known 3-hydroxysteroid oxidases are called "cholesterol oxidases" (enzymatically catalogued as E.C. #1.1.3.6) but cholesterol is only one of the 3-hydroxysteroid substrates, not the only one. The use of all 3-hydroxysteroid oxidases and the genes encoding such proteins, for the purpose of controlling insects, are within the scope of the present invention.

3-Hydroxysteroid oxidases are commercially available for use as reagents for serum cholesterol assays. For example, Sigma Chemical Company, St. Louis, Mo., offers three such 3-hydroxysteroid oxidases (denominated as cholesterol oxidases), one from a Streptomyces sp., one from a *Pseudomonas fluorescens*, and one from a Brevibacterium. Two other sources of 3-hydroxysteroid oxidase, two streptomycetes denominated A19241 and A19249, each of which produce a 3-hydroxysteroid oxidase, have been isolated. The organisms were collected in Madagascar. When these organisms were cultured according to usual methods the culture filtrates were found to affect insect larvae as described below.

A seed culture of A19249 was started in 55 mL sterile Tryptone-Yeast Extract broth, pH 6.8, in a 250 mL shake flask. The seed was agitated at 250 rpm on a rotary shaker for 3 days at 30° C. A New Brunswick Bioflo II Bioreactor with a 2 L working volume was filled with "medium 202" ($MgSO_4 \cdot 7H_2O$ 2 g/L, $KH_2PO_4$ 0.5 g/L, NaCl 0.5 g/L, $CaCO_3$ 1 g/L, $ZnSO_4 \cdot H_2O$ (1 mg/mL stock) 5 mL/L, 100 mM FeEDTA 0.5 mL/L, Soluble Starch 5 g/L, Dextrose 2.5 g/L, Malt Extract 2.5 g/L, Soytone 5 g/L). The pH was adjusted to 6.5 with 2.5 N NaOH or 1 N HCl, and 1 mL/L of P2000, an antifoam agent was added. The bio-reactor was sealed and autoclaved for 25 min at 250° C. The seed, at 3 days growth, was used to inoculate the fermentor at 2% or 40 mL. The fermentation took place at 30° C. with an airflow of 1 L/min and agitation running at 500 rpm. The fermentation was harvested after 40 h.

Each of these enzymes has demonstrated control of insects as shown below. The *P. fluorescens* 3-hydroxysteroid oxidase is immunologically distinct from the Streptomyces enzymes, but it also controls insects.

Other organisms producing 3-hydroxysteroid oxidases of the present invention may be identified by assaying culture filtrates or individual proteins for 3-hydroxysteroid oxidase activity using a spectrophotometric assay, described below, which measures hydrogen peroxide production in the presence of a 3-hydroxysteroid, for example, cholesterol [Gallo, 1981].

The plant-colonizing microorganisms of the present invention are useful in a method of combatting boll weevil and lepidopteran pests wherein an "insecticidally effective amount" of the plant-colonizing microorganism is applied to the plant environment or to the plant seed. When used as a seed coating, these microorganisms are applied to the plant seed prior to planting. The plant-colonizing microorganism will have the same spectrum of insecticidal activity and control of insects as the culture filtrates containing 3-hydroxysteroid oxidase as shown in the examples below. Thus, an "insecticidally effective amount" is understood to mean an amount sufficient for controlling insect infestation and is within the skill of the art to determine. Factors to be considered include, the plant species to be protected, pest to be controlled, method of planting, method of application to the plant environment, soil type, (e.g. pH, organic matter content, moisture content), and whether the plant-colonizing microorganism is applied in a viable or non-viable (e.g. inactivated) form.

Theoretically, a single insecticidal plant-colonizing microorganism of the present invention (e.g. one containing and able to express a 3-hydroxysteroid oxidase gene) is sufficient to control insect infestation because it can grow into a colony of clones of sufficient number to express insecticidal amounts of 3-hydroxysteroid oxidase. However, in practice due to varying environmental factors which may affect the survival and propagation of the microorganism, a sufficient number of bacteria should be provided in the plant environment to assure survival. For example, application of $10^3$ to $10^{10}$ bacteria per seed is sufficient to insure colonization on the surface of the roots by the microorganism.

An insecticidally effective amount of 3-hydroxysteroid oxidase is typically between about 0.2 to 200 nanograms of 3-hydroxysteroid oxidase per insect. At least 0.5 nanograms, preferably 1 to 100 nanograms of insecticidally active protein per insect is sufficient for controlling insect infestation. Such an insecticidally effective amount of 3-hydroxysteroid oxidase can alternatively be expressed as a ratio between parts per million of protein (3-hydroxysteroid oxidase) to fresh weight of plant material. For example, an insecticidally effective amount of 3-hydroxysteroid comprises from about one to one hundred parts per million (ppm) protein to fresh weight of plant material. A preferred range is between about one to ten ppm (e.g. 1–10 micrograms of protein per 0.1–1.0 grams fresh weight plant material).

Compositions containing the insecticidal plant-colonizing microorganisms of the invention are prepared by formulating the biologically active microorganism or inactivated/non-viable microorganisms containing 3-hydroxysteroid oxidase with adjuvants, diluents, carriers, etc. to provide compositions in the form of finely divided particulate solids, granules, pellets, wettable powders, dusts, aqueous suspensions or dispersions, and emulsions. Illustrative of suitable carrier vehicles are: solvents e.g., water or organic solvents and finely divided solids, e.g., kaolin, chalk, calcium carbonate, talc, silicates and gypsum.

Additionally, it is contemplated herein that the compositions of the invention will include encapsulated forms; e.g., the insecticidal plant-colonizing microorganism can be encapsulated within shell walls of polymer, gelatin, lipid and the like or other formulation aids as for example emulsifiers, dispersants, surfactants, wetting agents, anti-foam agents and anti-freeze agents may be incorporated into the insecticidal compositions in the event that such compositions will be stored for any period of time prior to use.

It is further contemplated that two or more insecticidally active plant-colonizing microorganisms may be combined in an insecticidal composition of the present invention. Such a composition may comprise genus, species or strain distinct microorganisms each individually engineered to produce 3-hydroxysteroid oxidase, or distinct microorganisms which have been engineered to produce 3-hydroxysteroid oxidase and another plant pest toxin, such as the *Bacillus thuringiensis* protein toxin, or some combination thereof. Also, the insecticidally active plant-colonizing microorganism compositions of the present invention may contain other known biologically active agents, as for example, a herbicide, fungicide, or other insecticide.

The application of insecticidal compositions containing the genetically engineered plant-colonizing microorganisms of this invention as the active agent (whether in viable or non-viable form) can be carried out by conventional techniques utilizing, for example, spreaders, powerduster, boom and hand sprayers, spray dusters and granular applicators.

BIOEFFICACY ASSAYS

Boll Weevil Larvae Bioassay

Assays for activity against boll weevil larvae are carried out by incorporating the test sample into a agar liquid diet similar to that for southern corn rootworm [Marrone et al., 1985]. The test sample is substituted for the 20% water component. Neonate larvae are allowed to feed on the diet and mortality and growth stunting are evaluated.

The results of the assays of the 3-hydroxysteroid oxidases identified above are given in Table 1. Protein concentrations were determined spectrophotometrically with BCA protein reagent [Smith et al., 1985].

TABLE 1

| Protein Source | μg/mL | mUnits[1] per mL | Boll Weevil % Mortality | Survivor Stunting |
|---|---|---|---|---|
| A19241 | 11 | 400 | 88 | |
| | 3.5 | 27 | 30 | Moderate |
| A19249 | 60 | 2100 | 60 | Severe |
| | 40 | 1400 | 70 | Severe |
| | 20 | 700 | 15 | Severe |
| | 15 | 525 | 5 | Moderate |
| | 10 | 350 | 10 | Moderate |
| | 5 | 175 | 10 | Slight |
| Sigma Strep. | 57 | 1614 | 100 | |
| | 19 | 528 | 100 | |
| | 4.6 | 129 | 4 | Slight |
| Sigma P. fluor. | 44 | 692 | 100 | |
| | 19 | 290 | 39 | Slight |
| | 3.5 | 55 | 0 | |
| Sigma Brevibac. | 100 | 1480 | 40 | Moderate |
| | 60 | 888 | 40 | Slight |

[1]One Unit will oxidize 1 μmole of cholesterol/min when assayed with [cholesterol] = 129 μM.

Lepidopteran Larvae Bioassay

Lepidopteran larvae were tested on artificial diet treated with the indicated amount of the A19249 3-hydroxysteroid oxidase (cholesterol oxidase) for six days. The results are shown in Table 2.

An extended test was performed with tobacco budworm larvae to test the effect of the stunting noted in the six-day test. Tobacco budworm eggs were added to artificial diet (as described above) containing either buffer or 100 ppm A19249 3-hydroxysteroid oxidase (cholesterol oxidase). After seven days, some mortality as compared to the controls was noted. Surviving larvae were moved to fresh diet (control or treated, as appropriate). Percent mortality (corrected for control mortality) is reported for the 7 day and 10 day periods in Table 2A. The corrected number of larvae was 23.

TABLE 2

| Insect | Stage | Dose (μg/mL) | Stunting |
|---|---|---|---|
| tobacco budworm | egg/lv | 30 | 0 |
| | lv | 100 | 86% |
| corn earworm | lv | 50 | 0 |

TABLE 2-continued

| Insect | Stage | Dose (μg/mL) | Stunting |
|---|---|---|---|
| | lv | 100 | 35% |
| fall army worm | lv | 30 | 0 |
| tobacco hornworm | lv | 30 | 0 |
| | lv | 100 | 30% |
| pink bollworm | lv | 50 | 0 |
| | lv | 100 | 30% |
| European cornborer | lv | 50 | 0 |
| | lv | 100 | 46% |
| beet armyworm | lv | 100 | 76% |
| black cutworm | iv | 100 | 68% |

TABLE 2A

| Interval (days) | Percent Mortality |
|---|---|
| 7 | 20 |
| 10 | 61 |
| 14 | 80 |

Boll Weevil Larval Age Difference Test

The diet incorporation study described above was performed to determine relative sensitivities of neonate and older (2nd instar) boll weevil larvae to the Sigma Streptomyces 3-hydroxysteroid oxidase (cholesterol oxidase). The mortality results shown in Table 3 reflect an eight-fold difference in susceptibility at six days exposure. This difference disappears after two weeks of exposure.

TABLE 3

| | $LC_{50}$ values (ppm in diet) | | |
|---|---|---|---|
| | 6 days | 12 days | 16 days |
| neonate | 8.3 | 5.3 | 4.8 |
| 2nd instar | 66.7 | 12.5 | 6.5 |

Boll Weevil Reproduction Test

3-Hydroxysteroid oxidases, in addition to lethal effects on larvae, will also affect the reproductive cycle of adult boll weevils, as demonstrated by the following experiment.

Pre-oviposition

Approximately 220 adult boll weevils, collected within 2 days of emergence, were divided into two groups. One was fed standard diet and the other was fed standard diet containing 48 ppm 3-hydroxysteroid oxidase from Sigma (Streptomyces). The adults were allowed to feed and mate for four days at which time mortality was determined. The results are reported in Table 4.

Oviposition study

These two groups of adults were then divided into two subgroups and individually placed on artificial, enzyme-containing or control bolls. Artificial bolls were constructed of standard diet, with or without 48 ppm 3-hydroxysteroid oxidase, and encased in paraffin containing 1% cottonseed oil. After three days at 27° C., the adults were removed and ten bolls from each of the four groups were removed and examined for eggs. The remaining bolls were incubated for an additional 7 days at 27° C. to allow development of larvae. The bolls were then dissected and the eggs and larvae, dead and surviving, were counted. The results are reported in Tables 5 and 6.

Group 1=Control Adults placed on control bolls

Group 2=Control Adults placed on treated bolls

Group 3=Enzyme-fed adults placed on control bolls

Group 4=Enzyme-fed adults placed on treated bolls

TABLE 4

|  | Initial # | Survivors |
|---|---|---|
| Adults fed control diet | 111 | 110 |
| Adults fed treated diet | 110 | 107 |

TABLE 5

|  | Bolls with eggs or larvae | No. of females |
|---|---|---|
| Group 1 | 20 | 29 |
| Group 2 | 17 | 26 |
| Group 3 | 9 | 27 |
| Group 4 | 2 | 17 |

TABLE 6

|  | Total number larvae | Number live larvae |
|---|---|---|
| Group 1 | 24 | 24 |
| Group 2 | 18 | 1 |
| Group 3 | 3 | 1 |
| Group 4 | 0 | — |

The above results confirm the effects of 3-hydroxysteroid oxidase on boll weevil larvae when apparently normal larvae are challenged with the enzyme in their diet. Data in Table 5 indicate that adults fed 3-hydroxysteroid oxidase do not oviposit normally, even when presented with control bolls. It is also apparent that normal adults will readily oviposit in bolls containing the enzyme (Table 5). Table 6 data suggest a reduction of egg viability when adults are fed 3-hydroxysteroid oxidase during the pre-oviposition period. Although no direct mortality in adults was observed (Table 4) during the observation period, there is evidence of profound 3-hydroxysteroid oxidase effects on the adults' ability to develop and/or oviposit viable eggs.

Mode of Action Studies

The following studies show that 3-hydroxysteroid oxidase has a direct effect on the insect itself and that the activity demonstrated in the experiments described above cannot be attributed to the enzymes effect on the insect's diet, for example by sterol depletion. Lepidopteran larvae and boll weevils are most susceptible to the enzyme. It is believed that this specificity is due to the effect of 3-hydroxysteroid oxidase on the midgut of the insect as explained in more detail below. It has been observed that the boll weevil midgut has a proteinase composition which is more like lepidopteran than that of coleopteran (Purcell, et al., 1992), which probably explains why boll weevils and lepidopteran are the most sensitive to the enzyme. Other insects with similar midgut physiologies may also be controlled by 3-hydroxysteroid oxidase. In addition, 3-hydroxysteroid oxidases other than those tested and reported herein may control a different spectrum of insects with different midgut physiologies.

Cotton Seed Diet Assay

The Southern corn rootworm diet used in the assay described above was the control. Two treatment diets were made by mixing 30 g of one of two types of cottonseed flour into 170 mL of a 1.6% agar solution at 50° C., containing 0.13% propionic acid, 0.014% phosphoric acid, and 30 mg each of streptomycin sulfate and chlortetracycline. Before mixing, 10% KOH was used to adjust the pH to 6.2. One test diet utilized raw cottonseed flour (Sigma) as the nutrient source; the other utilized Pharmamedia™ (Traders Protein), a flour made up of cottonseed embryos. The diets were incubated in a water bath at 40° C. Dilutions of the Sigma Streptomyces 3-hydroxysteroid oxidase (cholesterol oxidase) were incorporated into the diets as described above. Boll weevil larvae were allowed to feed and mortality rates were determined after six days. The results shown in Table 7 demonstrate that the enzyme is lethal to boll weevil larvae in the presence of cotton plant components.

TABLE 7

| Enzyme conc. (ppm) | Diet (% Corrected Boll Weevil Mortality) | | |
|---|---|---|---|
|  | Control | Cottonseed | Cotton embryo |
| 10 | 0* | 27* | 14* |
| 20 | 29** | 85** | 58** |
| 60 | 100 | 100 | 82*** |

\* = Slight survivor stunting
\*\* = Moderate survivor stunting
\*\*\* = Severe survivor stunting In addition, tobacco budworm larvae are 68% stunted when exposed to 3-hydroxysteroid oxidase (100 ppm) in cottonseed diet (made with Pharmamedia™ flour).

Homogenized cotton leaf tissue assay

In order to test 3-hydroxysteroid oxidase against boll weevil larvae in a host tissue diet environment, a study was conducted in which cotton leaf tissue was the only nutritional component of an agar-based diet. Two cotton leaves (each approx. 5 inches wide) with stems were homogenized at 50° C. into 170 mL of a 1.6% agar solution contain-ing 0.13% propionic acid, 0.014% phosphoric acid, and 30 mg each of streptomycin sulfate and chlortetracycline. Before addition of the leaves, 10% KOH was used to adjust the pH of the agar solution to 6.2. The leaf "diet" was allowed to cool to 40° C. Dilutions of cholesterol oxidase and a water control were incorporated into the leaf "diet", poured into insect diet trays and allowed to cool. Boll weevil eggs were added to the diet wells. The assay was evaluated six days later. The results shown in Table 8 demonstrate that the enzyme maintains its insecticidal activity in the presence of cotton leaf tissue. This illustrates that the enzyme is insecticidal in the presence of intact cotton tissue and cells. Since the sterols in these leaf homogenates would presumably not all be accessible to the exogenously added 3-hydroxysteroid oxidase, this suggests that the enzyme is not depleting the diet of all the necessary sterols and that the mode of action of 3-hydroxysteroid oxidase is not dependent on sterol depletion of the nutrient source. These results demonstrate that successful control of boll weevil should be attained when the 3-hydroxysteroid oxidase gene is expressed in cotton tissue.

TABLE 8

|  | Boll weevils | |
|---|---|---|
| cholesterol oxidase | Initial | Survivors |
| 10 ppm | 24 | 20 |
| 50 ppm | 24 | 12 |
| 100 ppm | 24 | 0 |

Activity of Cholesterol Oxidase on Cotton Callus Tissue.

Two experiments were performed using cotton callus as the assay feeding substrate. In both cases the arena was a 96-well insect diet tray; each well contained 0.5 mL of gelled 2% agar, with 0.13% propionic acid and 0.014% phosphoric acid, covered with a ½ inch filter paper disc. For each replicate, fifty to one hundred milligrams of cotton callus (Coker 312) was soaked in either water (control) or a 400 ppm cholesterol oxidase solution and placed in a diet tray well. A second instar boll weevil larva was added to each well, and the tray was covered with a sheet of mylar and sealed with a tacking iron. Assay duration was six days. The results shown in Table 9 demonstrate that the enzyme is active in cotton callus bioassays. This illustrates that the enzyme is insecticidal in the presence of intact cotton tissue and the bioactivity is seen when the enzyme is ingested with whole cotton cells and tissue. Since the sterols in this callus would presumably not all be accessible to the exogenously added 3-hydroxysteroid oxidase, this further demonstrates that the mode of action of 3-hydroxysteroid oxidase is not dependent on sterol depletion of the nutrient source. These results demonstrate that successful control of boll weevil should be attained when the 3-hydroxysteroid oxidase gene is expressed in cotton tissue.

TABLE 9

|  | Percent corrected boll weevil mortality (N) | |
| --- | --- | --- |
|  | 1st study | 2nd study |
| Enzyme soaked callus | 36 (12) | 54 (24) |

Comparison of Boll Weevil $LC_{50}$ Values for Various Diet Assays

The table below summarizes the activity of 3-hydroxysteroid oxidase on boll weevil neonate larvae when presented in various diets. If the activity depended upon depletion of sterols from the diet then one would expect that the amount of enzyme required for boll weevil mortality would depend greatly upon the diet that is utilized in the assay since the amount and accessibility of the constituent sterols would vary widely in these assay mediums. The data shown in Table 10 demonstrate that $LC_{50}$ values obtained are very consistent from one type of assay to the next. This further demonstrates that the mode of action of 3-hydroxysteroid oxidase is not dependent on sterol depletion of the nutrient source but that the enzyme is directly active upon the boll weevil. These results demonstrate that successful control of boll weevil should be attained when the 3-hydroxysteroid oxidase gene is expressed in cotton tissue.

TABLE 10

| Diets | LC50 (ppm) | 95% confidence limits |
|---|---|---|
| artificial diet | 20.9 | 16.2–29.5 |
| cottonseed embryo | 13.6 | 3.5–22.2 |
| cottonseed flour | 11.8 | 6.3–15.5 |
| cotton leaf | 18.4 | 14.8–23.5 |

Spectrum of Insecticidal Activity of 3-Hydroxysteroid Oxidase

Three other coleopteran species, three other insects, and one mite species were evaluated for susceptibility to Sigma Streptomyces 3-hydroxysteroid oxidase (Table 11). Bioassays were evaluated after 4 to 7 days to measure acute effects of the enzyme on the insects' growth and survival. No significant acute effects (mortality or stunting of larval growth) were observed in these short term assays. The long term effects of exposure to cholesterol oxidase were not determined for these insects. The bioactivity against tobacco budworm demonstrates that longer exposure to the enzyme resulted in greater mortality (Table 2*a*, above). Thus deleterious effects on larval growth and development of the insects listed in Table 11 and other insects may result from chronic ingestion of 3-hydroxysteroid oxidase. ("lv"=larvae)

TABLE 11

| Insect | Stage | Dose (μg/mL) | Mortality (stunting) |
|---|---|---|---|
| corn rootworm | egg/lv | 30 | 0 |
| | | 100 | 0 |
| Colorado potato beetle | lv | 100 | 13 |
| German cockroach | nymph | 75 | 0 |
| yellow fever mosquito | lv | 15 | 0 |
| green peach aphid | all stgs | 30 | 0 |
| | | 100 | 0 |
| two spot spider mite | adult | 150 | 0 |
| sugarcane rootstalk borer | lv | 100 | 0 |

Mode of Action Theory

While not being bound by this theory, it is believed that the 3-hydroxysteroid oxidase enzyme kills or stunts boll weevil larvae and stunts the growth of lepidopteran larvae by some action in the gut after ingestion. There are no lethal or stunting effects from feeding boll weevil or lepidopteran larvae a diet sample that was incubated for one week with a 3-hydroxysteroid oxidase and then boiled prior to using it in the above assay. This further demonstrates that the mode of action of 3-hydroxysteroid oxidase is not dependent on sterol depletion of the nutrient source but that the enzyme is directly active upon the insect.

Nor do cholestenone or hydrogen peroxide, the products of enzymatic action on cholesterol, exhibit any lethal effects against boll weevil when incorporated at up to 200 μM in the standard diet described above. The addition of catalase (E.C. #1.11.1.6) to 3-hydroxysteroid oxidase in the bioassay does not block the lethal effects of 3-hydroxysteroid oxidase on boll weevil, providing further evidence that in vitro generation of hydrogen peroxide is not the mode of action.

The enzymatic action in the gut is believed to be oxidation of the 3-hydroxysteroid(s) of the cell membranes in the lining of the gut. The effects of ingested 3-hydroxysteroid oxidase on the midguts of boll weevil larvae have been studied. The midguts of boll weevil larvae (neonate and second instar at initiation of assay) feeding on diets containing sublethal doses of 3-hydroxysteroid oxidase were dissected out. Representative midguts were immediately placed in fixative and analyzed microscopically for morphological changes. Disruption of the epithelial cell layer was observed in the guts of larvae ingesting low doses, and complete lysis of the cells was observed from the higher doses. There was a good correlation of the morphological changes with the observed mortality over the 3-hydroxysteroid oxidase concentration range in the diet. Parallel midguts were dissected and homogenized and found to contain active 3-hydroxysteroid oxidase in enzymatic assays. This study demonstrates that the mode of action of 3-hydroxy-steroid oxidase on insect larvae involves lysis of the epithelial cell layer, possibly by oxidation of its membrane cholesterol or other 3-hydroxysteroid.

Enzyme Identification

The active proteins from the Madagascar Streptomyces microorganisms were isolated, purified, partially sequenced, and identified as 3-hydroxysteroid oxidases.

Protein Isolation

Each culture filtrate was purified by first sizing on YM10 membranes (Amicon) to a [>10 kDa] fraction, followed by multiple chromatography runs on an FPLC Mono Q HR10/10 (Pharmacia LKB, Piscataway, N.J.) column. For chromatography on the Mono Q column, the samples were loaded on the column in 25 mM Hepes pH 7.5 and eluted with a gradient to 1.0 M KCl in 25 mM Hepes pH 7.5. Fractions were collected and aliquots of each were filtered through 0.2 µ Acrodisc syringe tip filters. Each was tested in the boll weevil assay described above. Aliquots of insecticidally active fractions were electrophoresed on SDS-PAGE [Laemmli, 1970]using a Daiichi Double Gel Device and 10–20% mini-gel. Proteins were visualized by silver staining using Daiichi silver stain reagent kit. The active enzymes of the present invention, isolated from the novel microorganisms, were found to be a 52.5 kDa protein.

Amino Acid Sequences

An SDS-PAGE gel of the protein produced by Streptomyces A19241, isolated as above, was blotted onto PVDF paper (Immobilon, Millipore Corp.) using the protocol of Matsudaira [Matsudaira, 1987]. The N-terminus was sequenced using automated Edman degradation chemistry. A gas phase sequencer (Applied Biosystems, Inc.) was used for the degradation using the standard sequencer cycle. The respective PTH-aa derivatives were identified by reverse phase HPLC analysis in an on-line fashion employing a PTH analyzer (Applied Biosystems, Inc.) fitted with a Brownlee 2.1 mm i.d. PTH-C18 column. For internal sequences, digestions were carried out on purified 3-hydroxysteroid oxidase from A19249 using trypsin (TPCK-treated, from Worthington Biochemicals Corp., Freehold, N.J.). Fragments were then purified by reverse phase HPLC and sequenced in an N-terminal fashion.

The resulting partial sequences were compared to known proteins and a strong (71%) homology was found with the reported fourteen amino acid sequence at the N-terminus of a 3-hydroxysteroid oxidase isolated from a Streptomyces species [Ishizaki et al., 1989]. The reported enzyme has an $M_r$ of 54.9 kDa which agrees well with the $M_r$ of 52.5 kDa of the isolated enzyme.

Six internal fragments of the purified enzyme from A19249, also having homology to six regions of the reported enzyme, were sequenced. The fragments had 95, 76, 64, 58, 89, and 100 percent sequence identifies.

Amino Acid Composition Determination and Comparison

The amino acid composition of the 3-hydroxysteroid oxidase produced by A19249 was determined and compared with the composition of the reported Streptomyces enzyme. The samples were subjected to acid hydrolysis (6N HCl, vapor phase hydrolysis using a Water's Picotag workstation, 24 hr, 110° C.). All analyses were performed after post-column derivation of the hydrolysates using ninhydrin [Moore et al., 1963]. A Beckman Model 6300 Auto analyzer was employed for the actual determinations. The S delta n/N statistic is used to compare two compositions in order to make a prediction about their relatedness. The formula for the statistic is:

$$\frac{1}{2}\Sigma(n_{Ai}-n_{Bi})^2/N$$

where A is one composition, B is the other composition, i is each amino acid, n is the number of each amino acid, N is the total number of amino acids in the protein. If S delta n/N is <0.42, then there is a greater than 95% chance that the proteins are related. The smaller the value, the more closely the determined compositions match.

The S delta n/N statistic for the A19249 protein compared to the reported enzyme is 0.36, indicating that the two are highly related.

3-Hydroxysteroid Oxidase Assay

The identity of the enzyme was confirmed by testing its ability to oxidize a 3-hydroxysteroid, specifically cholesterol. The enzyme is added to a reagent mixture comprising horseradish peroxidase (20 U/mL), phenol (14 mM), 4-amino antipyrine (0.82 mM), Triton® X-100 (0.05%) and phosphate buffer (100 mM, pH 7). The sterol in isopropanol is then added and the absorbance at 500 nm monitored. One unit of activity is defined as the amount of enzyme required to oxidize 1 μmole of sterol per minute at 20° C.

The activity levels of the enzymes are reported in Table 12 for 3-hydroxysteroids representative of various classes of 3-hydroxysteroids. The enzyme sources are as follows:

1=A19249

2=A19241

3=Sigma Streptomyces

4=Sigma Pseudomonas

TABLE 12

| | Relative Rate for Enzymes | | | |
|---|---|---|---|---|
| Sterol | 1 | 2 | 3 | 4 |
| cholesterol | 100 | 100 | 100 | 100 |
| dihydrocholesterol | 56 | 56 | 59 | 69 |
| dehydrocholesterol | 13 | 12 | 7 | 47 |
| lathosterol | 28 | 34 | 27 | 71 |
| stigmasterol | 22 | 28 | 11 | 21 |
| sitosterol | 88 | 65 | 49 | 50 |
| campesterol* | 65 | 64 | 45 | 49 |
| fucosterol | 22 | 20 | 12 | 68 |
| lanosterol | <1 | <1 | <1 | 1 |
| ecdysone | <1 | <1 | <1 | <1 |
| 20-OH ecdysone | <1 | <1 | <1 | <1 |

*65/35 mixture of campesterol and dihydrobrassicasterol

Immunological Comparison of Enzymes

The Sigma Streptomyces enzyme is immunologically related to the 3-hydroxysteroid oxidases produced by the isolates of the present invention, numbers A19241 and 19249, as demonstrated by Western blotting [Burnette et al., 1981]using polyclonal antisera generated against the Sigma Streptomyces enzyme. The antisera recognized both enzymes produced by the isolates. The 3-hydroxysteroid oxidase from *P. fluorescens* was not recognized by the antisera. This demonstrates that immunologically distinct 3-hydroxysteroid oxidases are lethal to boll weevils.

Genetic Identification

The 3-hydroxysteroid oxidase gene was isolated from one of the Streptomyces microorganisms isolated in Madagascar and its sequence determined.

Cloning of the 3-Hydroxysteroid Oxidase Gene from A19249

As discussed above, peptide sequences of purified 3-hydroxysteroid oxidase from Streptomyces sp. strain A19249 (hereinafter "A19249") were obtained for four regions of the protein. These peptide sequences were compared to a database of known protein sequences, and this comparison revealed that the A19249 protein showed a high degree of homology to a known 3-hydroxy-steroid oxidase from Streptomyces [Ishizaki]. Comparing the A19249 peptide sequences to this known protein sequence, these peptides were assigned to their likely positions in the A19249 protein sequence. The sequence derived from the intact 3-hydroxysteroid oxidase from A19249 corresponded to a region near the N-terminus of the secreted form of the enzyme from the published sequence. From this it was concluded that the A19249 N-terminal peptide sequence was also likely to correspond to a "mature" secreted form of the protein lacking its putative secretory signal sequence. This was later confirmed by the DNA sequence analysis of the A19249 gene (see below). Three peptides were used to construct hybridization probes for isolation of the A19249 3-hydroxysteroid oxidase gene. Peptide N2 (SEQ ID NO:1) corresponded to N-terminal amino acids 29–43 of the known mature protein sequence (sequence without the putative signal peptide); peptide C1 (SEQ ID NO:2) to amino acids 434–449 of the mature protein sequence; and peptide C2 (SEQ ID NO:3) to amino acids 464–475 of the mature protein sequence.

cloned into plasmid vector pUC18 [Yanisch-Perron et al., 1985]in both orientations for further analysis. Restriction mapping showed that there were internal SalI and BglII sites as predicted by the Southern hybridization analysis. These sites are also conserved compared to the pub-lished 3-hydroxysteroid oxidase gene sequence. The BamHI fragment was further subcloned into four fragments for direct DNA sequencing.

Sequence Analysis of the 3-Hydroxysteroid Oxidase Gene

A total of 1865 nucleotides of DNA sequence from the 2.2 kb BamHI fragment were determined by direct DNA sequence analysis of subclones of this fragment using the dideoxy chain termination method. This sequence is identified as SEQ ID NO:7. This DNA sequence contains noncoding flanking regions at both the 3' and 5' ends. Analysis of this DNA sequence revealed a single long open reading frame that encodes a secretory signal peptide and the mature 3-hydroxysteroid oxidase protein of 43 and 504 amino acids,

| N2 (SEQ ID NO: 1): | ValSerThrLeuMetLeuGluMetGlyGlnLeuTrpAsnGlnPro |
|---|---|
| C1 (SEQ ID NO: 2): | AlaPheAlaAspAspPheCysTyrHisProLeuGlyGlyCysValLeu |
| C2 (SEQ ID NO: 3): | AsnLeuTyrValThrAspGlySerLeuIleProGly |

Based on these peptide sequences, three long nondegenerate oligonucleotides, corresponding to 3-hydroxysteroid oxidase peptide sequences from A19249 were designed using Streptomyces preferred codons. The oligonucleotides N2 (SEQ ID NO:4), C1 (SEQ ID NO:5), and C2 (SEQ ID NO:6) correspond to the peptides N2, C1, and C2 described above.

respectively. It is 84.37% identical to the published 3-hydroxysteroid oxidase nucleotide sequence. The derived amino acid sequence is 81.685% identical to the published 3-hydroxysteroid oxidase sequence. It is identified as SEQ ID NO: 8. Examination of the A19249 DNA sequence and comparison to the N-terminal amino acid sequence of intact 3-hydroxysteroid oxidase from A19249 revealed that the

| N2 Probe (SEQ ID NO: 4) | gtgtccaccctgatgctggagatgggccagctgtggaaccagccc |
|---|---|
| C1 Probe (SEQ ID NO: 5) | gccttcgccgacgacttctgctaccacccgctcggcggctgcgtcctg |
| C2 Probe (SEQ ID NO: 6): | aacctctacgtgaccgacggttcgctgatcccgggt |

Probes N2 (SEQ ID NO:4), C1 (SEQ ID NO:5), and C2 (SEQ ID NO:6) were all used as hybridization probes on Southern blots of A19249 genomic DNA. All three probes hybridized to the same 2.2 kb band in BamHI digested DNA, but N2 (SEQ ID NO:4) hybridized to a different fragment than C1 (SEQ ID NO:5) and C2 (SEQ ID NO:6) did in SalI and BglII digests. This indicated that SalI and BglII cut within the coding sequence of the 3-hydroxysteroid oxidase gene from A19249, which was confirmed by DNA sequence analysis.

The 3-hydroxysteroid oxidase gene from A19249 was isolated using the three synthetic oligonucleotides as hybridization probes on a library of DNA fragments of A19249 DNA in a lambda phage vector. A library was made in lambda EMBL3 using partial-digest Mbo1 DNA fragments of A19249. These probes were used to screen approximately 72,000 lambda phage plaques from the primary library. Primary plaque screening was performed using N2 (SEQ ID NO:4) plus C2 (SEQ ID NO:6). A total of 12 recombinant plaques that hybridized to the N and C-terminal probes were picked and purified by a second round of hybridization screening with probes N2 (SEQ ID NO:4) and C2 (SEQ ID NO:6). Southern blot analysis revealed that, in five of six lambda clones analyzed, a 2.2 kb BamHI fragment hybridized to both the N and C-terminal probes. This result confirmed the earlier Southern hybridization analysis that indicated a 2.2 kb BamHI fragment contained the 3-hydroxysteroid oxidase gene. This 2.2 kb DNA fragment was A19249 gene encoded a protein that includes a signal peptide sequence, which is apparently cleaved during secretion of the protein from the cells. Thus the N-terminus of the mature protein from A19249 begins with Ser-Gly-Gly-Thr-Phe, identified as SEQ ID NO:12.

Genetic Transformation

A 3-hydroxysteroid oxidase gene can be isolated from novel organisms or may be obtained from known sources, such as the Rhodococcus sp. described by Long et al., in WO 90 05,788. This gene may then be used to transform bacterial cells or plant cells to enable the production of 3-hydroxysteroid oxidase and carry out methods of this invention. Examples of how this may be done with the gene of A19249 are given below.

Mutagenesis of the A19249 Gene

In order to incorporate the A19249 gene into vectors appropriate for expression of the 3-hydroxysteroid oxidase in heterologous bacterial or plant hosts, it was necessary to introduce appropriate restriction sites near the ends of the gene. The goals of this mutagenesis were to create cassettes that included the protein coding sequence with minimal noncoding flanking sequences and to incorporate useful restriction sites to mobilize these cassettes. Cassettes were designed that would allow mobilization of the intact coding sequence including the signal peptide or just the mature coding sequence. To incorporate these cassettes into appropriate bacterial or plant expression vectors, an NcoI restriction site was engineered at the N-terminus of the intact protein sequence or at the N-terminus of the mature protein sequence. A BamHI site was engineered just after the termination codon of the intact coding sequence. Three mutagenesis primers were designed to create these cassettes, as shown below. Mutagenesis with primer Chossn (SEQ ID NO:9) substituted three amino acids (MAT) for valine and asparagine at the N-terminus of the signal peptide of the intact protein and Chomnr (SEQ ID NO:10) added two amino acids (MA) at the N-terminus of the mature protein. This was necessary to allow incorporation of the NcoI restriction site. Mutagenesis with primer Cho3br (SEQ ID NO:11) incorporated a BamHI site at the 3' end of the coding sequence. Primers Chomnr and Cho3br were used to direct formation of the antisense strand of DNA.

TABLE 13

| Sample | Dose ppm | mU/ml | % Mortality |
|---|---|---|---|
| 1 | 250 | 1775 | 86*** |
| 2 | 75 | 533 | 64*** |
| 3 | 25 | 178 | 21** |
| 4 | 0 | 0 | 0 |

\* = Slight survivor stunting
\*\* = Moderate survivor stunting
\*\*\* = Severe survivor stunting Expression of 3-Hydroxysteroid Oxidase in Plant Colonizing Bacteria To control boll weevil and lepidopteran pests, it may be desirable to express 3-hydroxysteroid oxidase in a plant-

| | |
|---|---|
| Chossn (SEQ ID NO:9): | CTCAGGAGCA<u>CCATGG</u>CGACCGCACAC (NcoI site underlined) |
| Chomnr (SEQ ID NO:10): | GTGCCGCCGGAGG<u>CCATGG</u>GGGCGGTGGC (NcoI site underlined) |
| Cho3br (SEQ ID NO:11): | GCCCCGCCCGTC<u>GGATCC</u>GTCAGGAACCCG (BamHI site underlined) |

The resulting modified sequences were identified as SEQ ID NO:13 encoding for the intact protein and SEQ ID NO:14 for the mature protein.

Expression of 3-Hydroxysteroid Oxidase in E. coli

The NcoI-BamHI fragments containing either the intact protein coding sequence or the mature protein coding sequence were inserted into a vector designed for protein expression in E. coli, vector pKK233-2 (Pharmacia LKB, Piscataway, N.J.). pKK233-2 contains the IPTG-inducible trc promoter. The vector containing the intact (full length) protein coding sequence as modified (SEQ ID NO:13) is designated pMON20909. The vector containing the mature protein coding sequence as modified (SEQ ID NO:14) is designated pMON20907. E. coli XL1 Blue cells (Statagene, San Diego, Calif.) modified with pMON20909 expressed 3-hydroxysteroid oxidase at higher levels of enzymatic activity than cells modified with pMON20907. The protein was extracted and purified from 4 liters of IPTG-induced E. coli containing pMON20909. The soluble fraction from sonicated bacterial lysate was concentrated and dialyzed, and then partially purified by Mono Q chromatography to yield 11 units of 3-hydroxysteroid oxidase activity. Western blot analysis indicates that the signal sequence of the intact protein is cleaved in E. coli, but the exact site of cleavage was not determined. Analysis of the recovered protein showed a five-fold reduction in enzymatic activity relative to the A19249 protein, but the loss has not been explained by DNA sequencing which found no alterations that would explain loss of enzymatic activity in plant protoplasts or E. coli.

The recovered protein was used in artificial diet overlay assays to determine the effects on boll weevil viability. The dose response curve for activity against boll weevil, based upon enzymatic activity units, was very similar to that originally observed with the Streptomyces and A19249 enzymes. The results are shown in Table 13. In addition, the recovered protein was tested against tobacco budworm and resulted in 88% stunting at a dose of 100 μg/ml.

colonizing microorganism and then apply this microorganism to the plant environment or to the plant seed. As the boll weevil and/or lepidopteran feeds on the plant, it ingests a toxic dose (i.e., amount sufficient for controlling insect infestation) of 3-hydroxysteroid oxidase produced by the plant-colonizing microorganism. Examples of such plant-colonizing microorganisms which may be engineered to contain and express the 3-hydroxysteroid oxidase gene include bacteria from the genera Pseudomonas, Agrobacterium Rhizobium, Erwinia, Azobacter, Azospirrillum, Klebsiella, Alcaligenes, Bacillaceae, and Flavobacterium and such endophytes that inhabit the plant vasculature such as Clavibacter species. Surface and rhizosphere colonizing bacteria from the genus Pseudomonas, Agrobacterium, and Bacillus are preferred for use herein, especially preferred are P. Fluorescens, A. radiobacter and B. thuringiensis. The B. thuringiensis organisms may provide additional insecticidal activity as these bacteria, themselves, feed on the insects or insect larvae and produce distinct protein toxins effective against another spectrum of insect pests. Examples of suitable phylloplane colonizing bacteria are P. putida, P. syringae and Erwinia species.

The genetic engineering of such plant-colonizing microorganisms to contain and express a DNA sequence encoding 3-hydroxysteroid oxidase employs conventional techniques analogous to those set forth above for the transformation of plants. Briefly, the 3-hydroxysteroid oxidase structural coding sequences of the invention are operably joined to a microbial promoter to create a gene which may then be inserted into a transformation cassette which cassette is then employed to transform the target plant-colonizing microorganism. More specifically, the 5' and 3' ends of the mature or intact 3-hydroxysteroid oxidase coding sequences provided herein are modified, if necessary, and the sequences inserted into vectors able to integrate into the chromosome of the transformed plant-colonizing microorganism chosen or able to exist extrachromosomally in the transformed microorganism. For surface colonizers, the 3-hydroxysteroid oxidase gene may be inserted into a broad host range vector capable of replicating in the aforementioned Gram negative hosts. Examples of these vectors are pKT231 of the IncQ incompatibility group [Bagdasarian et al., 1981] or pVK100 of the IncP group [Knauf, 1982]. For endophytes, the 3-hydroxysteroid oxidase gene can be inserted into the chromosome by homologous recombination or by incorporation of the gene onto an appropriate transposon capable of chromosomal insertion in these endophytic bacteria. The chromosomal insertion of heterologous genes into, for example *B. thuringiensis* organisms is described in U.S. Pat. No. 5,229,112, Obukowicz et al., issued Jul. 20, 1993, PCT Publication No. W) 94/25611, published 10 November 1994, and in PCT Publication No. WO 95/02058, published 19 January 1995, which are incorporated herein by reference.

In one embodiment of the present invention, 3-hydroxysteroid oxidase is produced in microorganisms in conjunction with a *B. thuringiensis* (*B.t.*) protein toxin. The two different insecticidal proteins, when combined, will result insecticidal activity against a larger number of insect species such that control of more pest species can be achieved than can be achieved by using either protein individually and, possibly a frequency of insect resistance to either agent that is less than that obtained when using either protein individually.

A preferred embodiment comprises the production of both insecticidal agents (the *B.t.* protein toxin and 3-hydroxysteroid oxidase) in a Gram negative plant-colonizing microorganism such as *Pseudomonas fluorescens* or in the Gram positive organism such as *Bacillus thuringiensis*. For one skilled in the art, construction of genes and DNA vectors for the co-production of 3-hydroxysteroid oxidase and *B.t.* protein toxins can be achieved through standard molecular biological manipulations.

DNA fragments carrying mature or intact 3-hydroxysteroid oxidase coding sequences can be incorporated into previously described genetic elements that allow for the introduction of *B.t.* protein toxin genes into Gram negative plant colonizing microorganisms. A specific example uses the NcoI—BamHI gene cassettes from pMON20907 and pMON20909 which carry, respectively, the mature and intact coding regions of cholesterol oxidase, and which have been shown above to direct the production of 3-hydroxysteroid oxidase in the Gram negative bacterium *Escherichia coli*. These cassettes can be inserted, along with a *B.t.* protein toxin coding sequence, into a vector that allows for the stable integration of some or all of the vector sequences into the bacterial chromosome by homologous recombination. One example of such a vector is the transposition-deficient transposon Tn5-containing vectors referenced above (Obukowicz et al., 1986, *J. Bacteriol.* 168:982–989 and U.S. Pat. No. 5,229,112, Obukowicz et al., issued Jul. 20, 1993). Both genes are inserted such that transcription originating at the NPTII promoter located in the IS50L element will produce a polycistronic mRNA capable of being translated to produce both insecticidal proteins (cholesterol oxidase and *B.t.* protein toxin). Alternately, 3-hydroxysteroid oxidase and *B.t.* protein toxins can be engineered as separate monocistronic elements in the same or separate vectors. The two genes are then inserted into the chromosome of the plant colonizing microorganism via homologous recombination between the flanking IS50 elements in the vector and a Tn5 element, bearing homology to the vector in the region of the IS50 elements, that was previously transposed into the chromosome. This results in the replacement of internal sequences of the resident Tn5 element by the insecticidal protein genes on the Tn5derived element on the plasmid vector.

In a specific embodiment, the plasmid vector pMAP110, described in Obukowicz et al. (*J. Bacteriol.* 168: 982–989, 1986), is employed to introduce, by homologous recombination, the desired protein toxin gene(s) into a plant-colonizing microorganism. Briefly, the plasmid vector pMAP110 contains a neomycin phosphotransferase gene and a gene encoding a *B.t.* protein toxin from *B. thuringiensis* var. kurastaki strain HD-1 cloned downstream from the NPTII promoter sequence between two transposase defective IS50 elements. This vector is cleaved with the restriction enzymes BglII and BamHI to remove the NPTII coding sequence and allow for insertion of the 3-hydroxysteroid oxidase structural coding sequence between the NPTII promoter of the IS50L element and the *B.t.* protein toxin gene to form a polycistronic unit capable of expressing both insecticidal protein genes. It is understood by those of skill in the art that modification of one or more restriction enzyme sites that flank the 3-hydroxysteroid oxidase and/or *B.t.* protein toxin gene by site-directed mutagenesis or the use of oligonucleotide linkers or adaptors may be required to construct the desired vectors and are routine manipulations for one skilled in the art. For example, the NcoI restriction enzyme site at the 5' end of the 3'-hydroxysteroid oxidase gene can be modified to a BamHI or BglII site that will be compatible in ligation reactions with the BglII site immediately downstream from the NPTII promoter.

Alternately, a 3-hydroxysteroid oxidase gene, either alone or with a *B.t.* protein toxin gene, can be carried on a cosmid vector that can be transformed or conjugated into plant-colonizing microorganisms and maintained as an episomal element as described by Suslow and Jones (U.S. Pat. No. 4,940,840 issued Jul. 10, 1990).

In another preferred embodiment, the 3-hydroxysteroid oxidase and *B.t.* protein toxin genes are stably integrated into the chromosome of plant-colonizing microorganisms by the use of transposable elements. In one such example, the Tn5 transposable element containing a *B.t.* protein toxin gene, described by Obukowicz et al. (*Gene*, 1986, 45: 327–331), is employed.

Alternately, genes for 3-hydroxysteroid oxidase can be introduced into plasmids or the chromosome of *B. thuringiensis* strains such that the resulting strains produce 3-hydroxysteroid oxidase in addition to *B.t.* protein toxins. A preferred method of achieving said protein production involves integrating a 3-hydroxysteroid oxidase gene into the chromosome of *B. thuringiensis*. This can be achieved by incorporating a functional 3-hydroxysteroid oxidase gene into a transposable element that is able to transpose in *B. thuringiensis* such as Tn5401 or its derivatives as described by Baum (PCT Publication No. WO 95/02058, published 19, January 1995). The modified element is then allowed to transpose from a plasmid shuttle vector into the chromosomal DNA. As in the embodiments describing construction of vectors that facilitate homologous recombination as a mean for transforming plant-colonizing microorganisms to contain and express the protein toxin gene and gene combinations of the present invention, it is anticipated that vectors which facilitate transformation via transposable elements will similarly require routine modification of one or more restriction enzyme sites that flank the 3-hydroxysteroid oxidase or *B.t.* protein toxin genes by site- directed mutagenesis or the use of oligonucleotide linkers or adaptors to construct the desired vectors.

Alternately, the 3-hydroxysteroid oxidase gene can be inserted into the *B. thuringiensis* chromosome by homologous recombination using a vector that also carries a DNA fragment derived from, and homologous to, the *B. thuringiensis* chromosome. This region of homology allows for the subsequent integration of all or part of the vector, including the 3hydroxysteroid oxidase gene, into the *B. thuringiensis* chromosome. One such system for integration of foreign DNA into the *B. thuringiensis* chromosome using homologous recombination is pSB210.1 or any of its derivatives described by Kalman (PCT Publication number WO 94/25611, published 10 November 1994). In all of the above cases, elements necessary for the transcription and translation of the gene in the microorganism are included. Promoters, ribosome binding sites and transcriptional terminators derived from *B.t.* protein toxin genes are examples of genetic elements that can be used to achieve expression of 3-hydroxysteroid oxidase in *B. thuringiensis*.

In another method, 3-hydroxysteroid oxidase genes can reside on recombinant plasmid vectors in *B. thuringiensis*. For example, vectors such as those described for use in the site-specific recombination system derived from *B. Thuringiensis* transposon Tn5401 described by Baum (WO 95/02058, supra) can be used.

The recovered insecticidal plant-colonizing microorganism may be assayed in the standard artificial diet assay described in U.S. Pat. No. 5,229,112, supra.

All publications and patents mentioned in this specification are herein incorporated by reference as if each individual publication or patent was specifically and individually stated to be incorporated by reference.

From the foregoing, it will be seen that this invention is one well adapted to attain all the ends and objects hereinabove set forth together with advantages which are obvious and which are inherent to the invention.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

REFERENCES

Bagdasarian, M., Lurz, R., Ruckert, B., Franklin, F., Bagdasarian, M. M., and Timmis, K. N. "Specific purpose cloning vectors. II. Broad host range, high copy number RSF1010-derived vectors and a host vector system for gene cloning in Pseudomonas." *Gene*, 16:237–47, 1981.

Bevan, M. et al., *Nature*, 304:184, 1983.

Burnette, W. N. "Western blotting: Electrophoretic transfer of proteins from SDS-PAGE gels to unmodified nitrocellulose and radioiodinated detection with antibody and radioiodinated proteins." *Anal. Biochem.*, 112: 195–203, 1981.

Cornelissen, B. J. C., et al. *EMBO Journal*, 5: 37–40, 1986.

Fischhoff, D. A. and Perlak, F. J. "Synthetic plant genes and method for preparation." European Patent Application, Publication Number 0 385 962, 1990.

Gallo, L. L. "Pancreatic sterol ester hydrolase." *Methods Enzymol.*, 71: 665–7, 1981.

Herrera-Estrella, L. et al., *Nature*, 303:209, 1983.

Ishizaki, T., Hirayam, N., Shinkawa, H., Nimi, O., and Murooka, Y. "Nucleotide Sequence of the Gene for Cholesterol Oxidase from a Streptomyces sp." *Journal of Bacteriology*, 171: 596–601, 1989.

Kay, R. et al., *Science*, 236: 1299–1302, 1987.

Klee, H. J. et al., *Bio/Technology*, 3: 637–642, 1985.

Knauf, V. C. and Nester, E. "Wide host range cloning vectors: A.cosmid bank of an Agrobacterium Ti plasmid." *Plasmid*, 8: 43–54, 1982.

Laemmli, U. K. "Cleavage of structural proteins during the assembly of the head of bacteriophage T4." *Nature*, 227: 680–5, 1970.

Long, Susan, and Ostroff, Gary R. "Cloning and expression of cholesterol oxidase gene of Nocardioform bacteria." PCT Int. Appl. WO 90 05,788.

Marrone, P. G., Ferri, F. D., Mosley, T. R., and Meinke, L. J. "Improvements in laboratory rearing of the southern corn rootworm, Diabrotica undecimpunctata howardi Barber (Coleoptera: Chrysomelidae) on artificial diet and corn." Journal of Economic Entomology, 78: 290–3, 1985.

Matsudaira, P. "Sequence from picomole quantities of proteins electroblotted onto polyvinylidene difluoride membranes." *Journal of Biol. Chem.*, 261: 10035–38, 1987.

Moore, S. and Stein, W. H. "Chromatographic determination of amino acids by the use of automatic recording equipment." *Methods in Enzymology*, 6: 819–31, 1963.

Purcell, J. P., Greenplate, J. T., and Sammons, R. P. "Examination of midgut luminal proteinase activities in six economically important insects." *Insect Biochem. Molec. Biol.*, 22:41–47, 1992.

Schuler, M. A. et al., *Nucleic Acids Research*, 10: 8225–8244, 1982.

Smith, A. G., and Brooks, C. J. W. "Cholesterol oxidases: Properties and Applications." *Journal of Steroid Biochemistry*, 7: 705–713, 1976.

Smith, P. K., Krohn, R. I., Hermanson, G. T., Mallia, A. K., Gartner, F. H., Provenzano, M. D., Fujimoto, E. K., Goeke, M. N., Olson, B. J., and Klenk, D.C. "Measurement of protein using bicinchoninic acid." *Analytical Biochemistry*, 150: 76–85, 1985.

Winter et al. *Mol. Gen. Genet.*, 221(2): 315–19, 1988.

Yanisch-Perron, C., Viera, J., and Messing, J. "Improved M13 phage cloning vectors and host strains: nucleotide sequences of the M13mp18 and pUC19 vectors." *Gene*, 33: 103–19, 1985.

---

What is claimed is:

1. In a method of controlling plant insect pests by applying to the plant environment or plant seed an insecticidally effective amount of a protein toxin for ingestion by the insect, the improvement comprising applying to the plant environment or plant seed a plant-colonizing microorganism genetically engineered to contain and express a heterologous gene comprising a DNA sequence encoding 3-hydroxysteroid oxidase in an amount effective for controlling insect infestation, wherein the insect is a boll weevil or a lepidopteran.

2. The method of claim 1 wherein the DNA sequence encoding 3-hydroxysteroid oxidase is derived from a bacterial species selected from the group consisting of Streptomyces, Pseudomonas and Brevibacterium.

3. The method of claim 1 wherein the DNA sequence encoding 3-hydroxysteroid oxidase is derived from Streptomyces sp. strain A19249.

4. The method of claim 1 wherein the plant insect pests are in a larvae stage.

5. The method of claim 3 wherein the DNA sequence comprises SEQ ID NO: 13 or SEQ ID NO: 14.

6. The method of claim 5 wherein the plant-colonizing microorganism is selected from the genus Pseudomonas, Agrobacterium, Rhizobium, Erwinia, Azobacter, Azospirrillum, Klebsiella, Alcaligenes, Bacillaceae, Flavobacterium, and Clavibacterium.

7. The method of claim 5 wherein the plant-colonizing microorganism is selected from the genus Pseudomonas, Agrobacterium, and Bacillus.

8. The method of claim 7 wherein the plant-colonizing microorganism is applied to the plant environment.

9. The method of claim 7 wherein the plant-colonizing microorganism is applied to the seed.

10. The method of claim 8 wherein the amount effective for controlling insect infestation is from one ppm to 100 ppm of protein toxin per fresh weight of plant material.

11. The method of claim 8 wherein the amount effective for controlling insect infestation is from 0.2 nanograms to 200 nanograms of protein toxin per insect.

12. A composition for use in controlling insect infestation of a plant, the composition comprising a genetically transformed plant-colonizing microorganism capable of expressing in a plant environment an insecticidally effective amount of 3-hydroxysteroid oxidase.

13. The composition of claim 12 wherein the genetically transformed plant-colonizing microorganism is selected from the genus Pseudomonas, Agrobacterium, Rhizobium, Erwinia, Azobacter, Azospirrillum, Klebsiella, Alcaligenes, Bacillaceae, Flavobacterium, and Clavibacterium.

14. The composition of claim 13 wherein the genetically transformed plant-colonizing microorganism is from the genus Pseudomonas or Bacillus.

15. The composition of claim 14 wherein the plant environment is the rhizosphere or the plant surface.

16. The composition of claim 14 wherein the plant environment is the plant seed.

17. A genetically transformed plant-colonizing microorganism comprising a heterologous gene comprising a promoter operable in the microorganism and a structural DNA sequence encoding 3-hydroxysteroid oxidase.

18. The genetically transformed plant-colonizing microorganism of claim 17 wherein said microorganism is from the genus Pseudomonas or Bacillus.

19. The genetically transformed plant-colonizing microorganism of claim 18 wherein said microorganism is a *P. fluorescens*.

20. The genetically transformed plant-colonizing microorganism of claim 18 wherein said microorganism is a *B. thuringiensis*.

21. The genetically transformed plant-colonizing microorganism of claim 18 further comprising a *B. thuringiensis* protein toxin gene.

* * * * *